United States Patent [19]

Solomon et al.

[11] Patent Number: 4,816,458

[45] Date of Patent: Mar. 28, 1989

[54] METHOD OF TREATING HYPERPLOLIFERATIVE SKIN DISEASE WITH SUBSTITUTED-2,3,-DIHYDRO-6-SUBSTITUTED-PYRIMIDO[2,1]-PURINE-4,8(1H,9H)DIONES

[75] Inventors: Daniel M. Solomon, Edison; James J. Kaminski, Long Valley, both of N.J.

[73] Assignee: Schering Corporation, Kenilworth, N.J.

[21] Appl. No.: 945,103

[22] Filed: Dec. 19, 1986

Related U.S. Application Data

[63] Continuation-in-part of Ser. No. 732,994, May 13, 1985, Pat. No. 4,666,914.

[30] Foreign Application Priority Data

May 12, 1986 [WO] PCT Int'l Appl. ............... PCT/US86/01004

[51] Int. Cl.$^4$ ................... A61K 31/505; C07D 487/14
[52] U.S. Cl. ....................................... 514/267; 544/251
[58] Field of Search ...................... 544/251; 514/267

[56] References Cited

U.S. PATENT DOCUMENTS

| | | | |
|---|---|---|---|
| 3,862,189 | 1/1975 | Schwender | 544/265 X |
| 4,457,919 | 7/1984 | Simon et al. | 544/265 X |
| 4,460,590 | 7/1984 | Möller | 544/265 X |
| 4,569,936 | 2/1986 | Blythin | 514/267 |
| 4,666,914 | 5/1987 | Solomon et al. | 514/267 |

OTHER PUBLICATIONS

Fieser, et al., "Reagents for Organic Synthesis", John Wiley & Sons, New York, (1967), pp. 588–589.
Fieser, et al., "Reagents for Organic Synthesis", John Wiley & Sons, New York (1974), p. 293.

*Primary Examiner*—Donald G. Daus
*Assistant Examiner*—D. G. Rivers
*Attorney, Agent, or Firm*—Richard C. Billups; James R. Nelson; Stephen I. Miller

[57] ABSTRACT

Substituted 2,3-dihydro-6-substituted-pyrimido[2,1-f]purine-4,8(1H,9H)-diones, their tautomers and salts, are disclosed for use as antihyperproliferative skin disease agents.

Methods for their preparation and use are described.

11 Claims, No Drawings

METHOD OF TREATING HYPERPLOLIFERATIVE SKIN DISEASE WITH SUBSTITUTED-2,3,-DIHYDRO-6-SUBSTITUTED-PYRIMIDO[2,1]-PURINE-4,8(1H,9H)DIONES

CROSS REFERENCE TO RELATED APPLICATION

This application is a continuation-in-part of U.S. application Ser. No. 732,994, filed May 13, 1985, now U.S. Pat. No. 4,666,914, priority of which is claimed hereunder.

BACKGROUND OF INVENTION

The present invention relates to substituted 2,3-dihydro-6-hydroxy-pyrimido[1,2-f]purine-4,8(1H,9H)-diones and tautomers thereof, and use of these compounds for the treatment of hyperproliferative skin disease. These compounds are also useful as anti-inflammatory agents for treating inflammatory conditions such as arthritis, spondylitis, and tendonitis in mammals, and are useful as anti-allergy agents for treating allergy-caused diseases. U.S. Pat. No. 4,569,936, issued to Blythin on Feb. 11, 1986 discloses certain related compounds having a 2-oxo substituent but fails to address the 2-dihydro compounds described herein.

SUMMARY OF INVENTION

This invention encompasses a method of treating hyperproliferative skin disease in a mammal comprising administering an anti-hyperproliferative skin disease effective amount of a compound having structural formula I

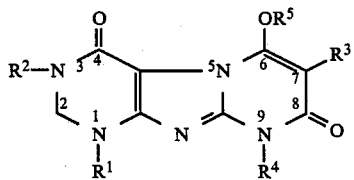

or a tautomer, pharmaceutically acceptable salt or hydrate thereof, wherein:

$R^1$ and $R^2$ are each independently hydrogen, cycloalkyl having from 3 to 8 carbon atoms, phenyl, lower alkyl, substituted phenyl, and lower alkyl substituted with cycloalkyl having from 3 to 8 carbon atoms, phenyl, thienyl or substituted phenyl;

$R^3$ is hydrogen, formyl, cycloalkyl having from 3 to 8 carbon atoms, alkenyl having from 2 to 8 carbon atoms (which may be substituted with up to 6 fluorines), alkynyl having from 3 to 8 carbon atoms, cycloalkenyl having from 5 to 8 carbon atoms, acyloxyalkyl having from 2 to 12 carbon atoms, —X—$R^6$ {wherein X is O, N or S and $R^6$ is phenyl, substituted phenyl, lower alkyl, or lower alkyl substituted with phenyl or cycloalkyl having from 3 to 8 carbon atoms}, —alkyl—Y—$C_pH_{2p+1}$ (wherein the alkyl portion has 1 to 6 carbon atoms, p is an integer from 0 to 4, and Y represents CO, O, S, $S^+$—$O^-$, $SO_2$ or —$NHC_2H_{2r+1}$ where r is an integer from 0 to 4), —$(CH_2)$—$_nCONR^7R^8$ (wherein $R^7$ and $R^8$ are independently hydrogen or lower alkyl and n is an integer from 0 to 6), —$(CH_2)_m$—$COOR^9$ (wherein $R^9$ is hydrogen or lower alky and m is an integer from 0 to 6), phenyl, substituted phenyl, lower alkyl or substituted lower alkyl {substituted with hydroxy, sulfhydryl, cyano, amino, halo, cycloalkyl having from 3 to 8 carbon atoms, phenyl, thienyl or substituted phenyl};

$R^4$ is hydrogen, phenyl, alkylphenyl, thienyl, substituted thienyl, pyridinyl, substituted benzyl, substituted phenyl or lower alkyl substituted with cycloalkyl having from 3 to 8 carbon atoms, phenyl, pyridinyl, thienyl or substituted phenyl;

and $R^5$ is selected from hydrogen and alkyl having from 1 to 4 carbon atoms.

A preferred embodiment of the invention is the method described above wherein the compound administered is a compound having the structural formula I or a pharmaceutically acceptable salt thereof, wherein $R^1$ and $R^2$ are independently selected from alkyl having from 1 to 4 carbon atoms;

$R^3$ is hydrogen, alkenyl having from 2 to 8 carbon atoms which may be substituted with up to 6 fluorines, alkynyl having from 3 to 8 carbon atoms, cycloalkenyl having from 5 to 8 carbon atoms, lower alkyl, or lower alkyl substituted with phenyl;

$R^4$ is lower alkyl substituted with phenyl, thienyl or substituted phenyl; and $R^5$ is hydrogen.

A more preferred method of treating hyperproliferative skin disease is administering the compound described above wherein $R^1$ and $R^2$ are alkyl having 1 to 3 carbon atoms, and in particular, methyl.

Another preferred method of treating hyperproliferative skin disease is administering a compound as described above wherein the group $R^3$ is hydrogen, alkenyl having from 3 to 8 carbon atoms which may be substituted with up to 6 fluorines, alkynyl having from 3 to 8 carbon atoms, cycloalkenyl having from 5 to 8 carbon atoms, lower alkyl, and lower alkyl substituted with phenyl. Most preferably $R^3$ is hydrogen, methyl, n-propyl, 2-propynyl, 2-propenyl, trans-2-butenyl, 2-cyclohexenyl, —$CH_2CH$=$C(CH_3)_2$(prenyl), —$CH_2CH$=$C(CF_3)CH_3$, —$CH_2CH$=$C(CF_3)_2$ and benzyl.

Another preferred method of treating hyperproliferative skin disease comprises administering the compound described above wherein $R^4$ is benzyl, 2-thienylmethyl or substituted benzyl; most preferably $R^4$ is 2-thienylmethyl, benzyl or p-fluorobenzyl.

Another preferred method as described above administering a compound of formula I wherein $R^5$ is hydrogen or one equivalent of a pharmaceutically acceptable metal cation, most preferably the sodium cation.

Particularly preferred compounds for use in the treatment of hyperproliferative skin disease having structural formula I are as follows:

9-benzyl-2,3-dihydro-1,3-dimethyl-6-hydroxy-7-propyl-pyrimido[2,1-f]purine-4,8(1H,9H)-dione;

2,3-dihydro-1,3-dimethyl-9-(4-fluorobenzyl)-6-hydroxy-7-propyl-pyrimido[2,1-f]purine-4,8(1H,9H)-dione;

9-benzyl-2,3-dihydro-1,3-dimethyl-6-hydroxy-7-(3-methyl-2-butenyl)-pyrimido[2,1-f]purine-4,8(1H,9H)-dione;

9-benzyl-2,3-dihydro-1,3-dimethyl-6-hydroxy-pyrimido[2,1-f]purine-4,8(1H,9H)-dione;

2,3-dihydro-1,3-dimethyl-9-(4-fluorobenzyl)-6-hydroxy-7-(3-methyl-2-butenyl)-pyrimido[2,1-f]purine-4,8(1H,9H)dione;

9-benzyl-2,3-dihydro-1,3-dimethyl-6-hydroxy-7-methylpyrimido[2,1-f]purine-4,8(1H,9H)-dione;

2,3-dihydro-1,3-dimethyl-9-(4-fluorobenzyl)-6-hydroxypyrimido[2,1-f]purine-4,8(1H,9H)-dione;

7,9-dibenzyl-2,3-dihydro-1,3-dimethyl-6-hydroxypyrimido[2,1-f]purine-4,8(1H,9H)-dione;
9-benzyl-2,3-dihydro-1,3-dimethyl-7-formyl-6-hydroxypyrimido[2,1-f]purine-4,8(1H,9H)-dione;
2,3-dihydro-1,3-dimethyl-9-(4-fluorobenzyl)-6-hydroxy-7-(2-propenyl)-pyrimido[2,1-f]purine-4,8(1H,9H)-dione;
9-benzyl-2,3-dihydro-1,3-dimethyl-7-(2-propynyl)-6-hydroxy-pyrimido[2,1-f]purine-4,8(1H,9H)-dione;
9-benzyl-7-(trans-2-butenyl)-2,3-dihydro-1,3-dimethyl-6-hydroxy-pyrimido[2,1-f]purine-4,8(1H,9H)-dione;
9-benzyl-7-(3-cyclohexenyl)-2,3-dihydro-1,3-dimethyl-6-hydroxy-pyrimido[2,1-f]purine-4,8(1H,9H)-dione;
9-benzyl-2,3-dihydro-1,3-dimethyl-7-ethoxycarbonylmethyl-6-hydroxy-pyrimido[2,1-f]purine-4,8(1H,9H)-dione;
9-benzyl-1,3-dimethyl-6-hydroxy-7-(3-trifluoromethyl-2-butenyl)-2,3-dihydropyrimido[2,1-f]purine-4,8(1H,9H)-dione;
2,3-dihydro-1,3-dimethyl-9-(2-thienylmethyl)-6-hydroxy-7-propyl-pyrimido[2,1-f]purine-4,8(1H,9H)-dione; and
2,3-dihydro-1,3-dimethyl-9-(4-methoxybenzyl)-6-hydroxy-7-(3-methyl-2-butenyl)-pyrimido[2,1-f]purine-4,8(1H,9H)-dione.

The above compounds are also preferred for the treatment of hyperproliferative skin disease in the form of their sodium salts. In the above list the compounds are named for convenience as their 6-hydroxy-8-one tautomers, but the equivalent 8-hydroxy-6-one tautomers are equally useful.

The present invention includes administering to a mammal an antihyperproliferative skin disease effective amount of a compound of formula I in the form of a pharmaceutical composition comprising a compound of formula I in combination with a pharmaceutically acceptable carrier.

As utilized herein, the terms listed below have the following definition unless otherwise indicated:

halogen and halo—fluorine, chlorine, bromine and iodine;
alkyl—(including the alkyl portion of alkoxy and of acyloxyalkyl) straight or branched saturated carbon chain of from 1 to 12 carbons with all substitutable carbons in the carbon chain as possible points of substitution;
lower alkyl—a subset of alkyl which is straight or branched chain alkyl of from 1 to 6 carbons, e.g. methyl, ethyl, propyl, isopropyl, butyl, t-butyl, 2,2-dimethylpropyl, pentyl, hexyl and the like;
alkenyl—straight or branched carbon chain of from 2 to 12 carbon atoms and containing at least one carbon to carbon double bond;
alkynyl—straight or branched carbon chain of from 2 to 12 carbon atoms and containing at least one carbon to carbon triple bond;
substituted phenyl—phenyl substituted with from 1 to 3 groups independently selected from halogen, trifluoromethyl, $—CONH_2$, $—CO_2H$, hydroxy, $—S(O)_aR^{10}$ wherein $R^{10}$ is lower alkyl and a is 0, 1 or 2, $—OR^{11}$ wherein $R^{11}$ is lower alkyl, or $—COR^{12}$ wherein $R^{12}$ is lower alkyl or alkoxy having from 1 to 6 carbon atoms;
substituted pyridinyl—pyridinyl substituted with from 1 to 3 groups independently selected from halogen, trifluoromethyl, $—CONH_2$, $—CO_2H$, hydroxy, $—S(O)_aR^{10}$ wherein a and $R^{10}$ are as previously defined, $—OR^{11}$ wherein $R^{11}$ is as previously defined and $—COR^{12}$ wherein $R^{12}$ is as previously defined;
substituted thienyl—thienyl substituted at positions 2, 3, 4 or 5 with from 1 to 3 groups independently selected from halogen, trifluoromethyl, $—CONH_2$, $—CO_2H$, hydroxy, $—S(O)_aR^{10}$ wherein a and $R^{10}$ are as previously defined, $—OR^{11}$ wherein $R^{11}$ is as previously defined and $—COR^{12}$ wherein $R^{12}$ is as previously defined;
cycloalkyl—non-aromatic carbocyclic ring having from three to ten carbon atoms with each substitutable carbon a possible point of substitution with lower alkyl, alkenyl, alkynyl, halogen, hydroxy, phenyl, substituted phenyl, sulfhydryl, cyano, amino, thienyl, substituted thienyl, pyridinyl or substituted pyridinyl;
cycloalkenyl—non-aromatic carbocyclic ring having from three to ten carbon atoms and at least one carbon to carbon double bond, with each substitutable carbon a possible point of substitution with lower alkyl, alkenyl, alkynyl, halogen, hydroxy, phenyl, substituted phenyl, sulfhydryl, cyano, amino, thienyl, substituted thienyl, pyridinyl or substituted pyridinyl;
substituted benzyl—benzyl substituted at positions 2, 3, 4 or 5 with halogen, trifluoromethyl, $—CONH_2$, $—CO_2H$, hydroxy, $—S(O)_aR^{10}$, where a and $R^{10}$ are as previously defined $—OR^{11}$ where $R^{11}$ is as previously defined and $—COR^{12}$ where $R^{12}$ is as previously defined;
acyl (including the acyl portion of acyloxyalkyl)—radicals derived from organic acids by the removal of the hydroxyl group, preferably from alkanoic acids;
amino— $—NH_2$, $—NH(A)$ and $—N(A)(B)$ wherein A and B are independently alkyl, alkenyl, alkynyl, cycloalkyl, alkoxy, cycloalkenyl, phenyl, substituted phenyl, pyridinyl, substituted pyridinyl, benzyl, substituted benzyl, thienyl, substituted thienyl or halo.
pharmaceutically acceptable metal and amine cations—lithium, sodium, potassium, magnesium, calcium, aluminum, zinc, iron, copper, gold, ammonium, ethylenediamine, mono-, di- and tri-ethanolamine, ethyldiethanolamine, n-butylethanolamine, 2-amino-2-methyl-1-propanol, tris(hydroxymethyl)-aminomethane, lysine, galactamine, N-methyl-glucosamine and the like.

DETAILED DESCRIPTION

Certain compounds used in the method of the invention may exist in isomeric forms. The invention contemplates treatment with all such isomers both in pure form and in admixture, including racemic mixtures.

The compounds of formula I used herein can exist in unsolvated as well as solvated forms, including hydrated forms, e.g, hemihydrate. In general, the solvated forms, with pharamaceutically acceptable solvents such as water, ethanol and the like are equivalent to the unsolvated forms for purpose of the invention.

Compounds of the formula I wherein $R^5$ is hydrogen may exist in tautomeric forms:

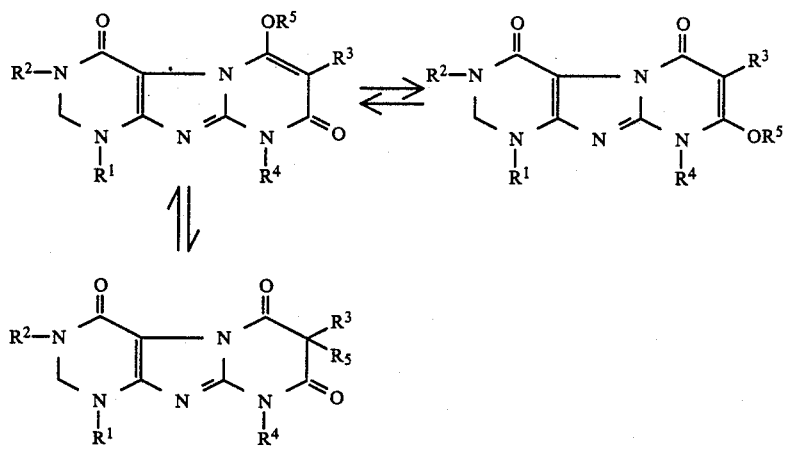

Such tautomeric forms are equivalent for purposes of the invention.

Certain compounds of formula I are acidic in nature, e.g. those compounds which possess a carboxyl or phenolic hydroxyl group. These compounds may form pharmaceutically acceptable salts. Examples of such salts are the sodium, potassium, calcium, aluminum, copper, gold and silver salts. Also contemplated is the use of a salt formed with a pharmaceutically acceptable amine such as ammonia, alkyl amine, hydroxyalkylamine, N-methylglucamine and the like.

Certain basic compounds of formula I also form pharmaceutically acceptable salts, e.g, acid addition salt and quaternary ammonium salts. For example, if substituent N atoms are present, the substituent nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The quaternary ammonium salts are prepared by conventional methods, e.g, by reaction of a tertiary amino group in a compound of formula I with a quaternizing compound such as an alkyl iodide, etc. The free base forms differ from their respective salt forms somewhat in certain physical properties, such as solubility in polar solvents, but the salts are otherwise equivalent to their respective free base forms for purposes of the invention.

The compounds of formula I may also form quaternary salts at an aromatic ring nitrogen atom.

All such acid, base and quaternary salts are intended to be pharmaceutically acceptable salts, and all acid and base salts are considered equivalent to the free forms of the corresponding compounds for purposes of treating hyperproliferative skin disease.

As used herein, hyperproliferative skin disease means any condition a symptom of which is accelerated skin cell production resulting in erythema, flakes, scales, plaques or papular lesions on the skin. Representative examples of hyperproliferative skin disease include psoriasis, eczema, dandruff and the like. Effectiveness of the compound of formula I for the treatment of hyperproliferative skin disease may be demonstrated by the Croton Oil Mouse Ear Test, as described in detail below.

Application of croton oil to the skin of a test mammal serves as an appropriate model for measuring the effects of compounds used in treating hyperproliferative skin disease. By measuring the weight of the skin to which croton oil is applied in the presence of a test compound and comparing to a control wherein croton oil is applied without the test compound, the inhibitory activity of the test compound is evaluated.

CROTON OIL MOUSE EAR TEST PROCEDURE

Male Charles River bred mice (strain $CD_1$) weighing 22–26 g are caged 8/group and acclimated for 4 days at controlled temperature with water and food ad lib prior to use.

Croton oil 0.6 ml (Amend Drug and Chemical Company, Irvington, N.J.) is dissolved in a vehicle comprising pyridine (24 ml), distilled water (6 ml) and diethyl ether (90 ml) to make a 0.5% solution.

Test compounds are weighed on a Cahn Millibalance and dissolved in the croton oil preparation, freshly prepared in glass vials 30 minutes or less prior to application, and placed in a tray filled with crushed ice.

Using an Oxford 10 microliter pipette, the compound in croton oil solution is applied to the inner surface of both ears of the mouse. Other groups receive croton oil or vehicle alone. Five hours after application the animals are sacrificed by $CO_2$ suffocation in a bucket using dry ice. A 6 mm dermal punch is used to biopsy both ears. The ear punches are then individually weighed on a Cahn Millibalance and weights recorded to the nearest 0.1 mg.

Data analysis indicates that the compounds of formula I are useful for the treatment of hyperproliferative skin disease. For example, the compound 9-benzyl-2,3-dihydro-1,3-dimethyl-6-hydroxy-7-(3-methyl-2-butenyl)-pyrimido[2,1-f]purine-4,8(1H,9H)dione reduces inflammation by 41% at a dose of 1 mg applied topically per ear.

The compounds of this invention are also useful to treat inflammation. For example, inflammatory conditions which can be treated include arthritis, spondylitis, tendonitis and the like.

The anti-inflammatory activity of the compounds of the invention may be demonstrated by the procedures described below.

The Reversed Passive Arthrus Reaction (RPAR) Test serves as a general screening test for compounds which have antiinflammatory activity under acute inflammatory conditions. The Chronic Adjuvant Athritic Rat (AAR) Test simulates the inflammatory disease process in man. The compounds of the invention are tested prophylactically, i.e., administered prior to inducing inflammation, and also subsequent to inducing inflammation. In this manner anti-inflammatory activity of the compounds of formula I is assessed.

RPAR Synovitis Technique

A Lewis rat is dosed orally with drug or placebo one hour prior to intravenous administration of 2.28 mg of bovine serum albumin (BSA) in 0.2 cc of pyrogen-free saline followed by the intraarticular injection of 0.54 mg of rabbit anti-BSA antibody in 0.03 cc of pyrogen-free saline into one knee joint. The contralateral knee is injected with 0.03 cc of pyrogen free saline. All injections are made with the animal under light ether anesthesia. Three hours later the rat is again dosed orally with drug or placebo. All drug doses are split. That is, one-half of the dose is administered before lesion induction and one-half is administered after lesion induction.

The following morning (about 17 hours after lesion induction) the rat is killed and both knee joints are exposed. The subpatellar areolar tissue with attendant synovium is excised and weighed. Differences between the weight of antibody and saline injected knees are considered to represent the inflammatory response for each animal (delta synovial weight). Differences in delta synovial weight between lesion controls and drug-treated rats are evaluated for statistical significance with an analysis of variance. Relative potencies are determined with a linear regression analysis.

Prophylactic Adjuvant-Induced Arthritis in Rats (AAR)

Groups of 10 male Lewis rats (from Charles River Laboratories, Ma.), weighing 150–170 grams are sensitized by subplantar injection in the left hind paw with 0.1 ml Freund's complete adjuvant enriched with heat-killed tuberculin bacilli. Hind paw volumes are determined with a mercury plethysmograph from Day 0 to Day 21 of the study. Differences in paw volume on Day 0 and 21 are recorded as the delta ($\Delta$) paw volume. In sensitized rats the injected hind paw increases in size by Day 2 and seven days later a similar response is seen in the contralateral hind paw. Differences in body weights on Day 0 and Day 21 are recorded as the delta ($\Delta$) body weight gain.

Daily oral doses of the drug suspended in methylcellulose or of methylcellulose alone are administered. In the chronic prophylactic assay, a compound of formula I is administered prior to antigenic challenge with tuberculin bacilli. In the chronic therapeutic assay, a compound of formula I is administered after inflammation has been induced with tuberculin bacilli, thereby simulating therapeutic use of the compound for the treatment of an inflammatory condition, e.g. arthritis.

The compounds of this invention are also useful for the treatment of allergy-caused diseases, such as chronic obstructive lung diseases. Chronic obstructive lung disease as used herein means disease conditions in which the passage of air into and out of the lungs is obstructed or diminished such as is the case in asthma, bronchitis and the like.

When administered for the treatment of hyperproliferative skin disease, the compounds may be administered topically or systemically. When administered topically, the amount of compound administered varies widely with the amount of skin being treated, as well as with the concentration of active ingredient applied to the affected area. For topical administration, a compound of formula I may be administered in a concentration ranging from about 0.001% to about 10%, preferably from about 0.01% to about 5%, applied several times daily to the skin. When used systemically, the compound may be administered orally, rectally or parenterally. When administered orally, the compounds of formula I are effective for the treatment of hyperproliferative skin disease at doses ranging from about 0.1 mg to about 100 mg, which may be administered in divided doses. When administered rectally, the compounds of formula I may be administered in doses ranging from about 0.1 mg to about 1000 mg. When administered parenterally, the compounds of formula I are effective for the treatment of hyperproliferative skin disease in doses ranging from about 0.05 mg/kg body weight to about 50 mg/kg body weight which may be administered in divided doses taken at 4 to 12 hour intervals.

For preparing pharmaceutical compositions from the compounds described herein, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to about 70 percent active ingredient on a weight/weight basis. Suitable solid carriers are magnesium carbonate, magnesium stearate, talc, sugar, lactose, pectin, dextrin, starch, gelatin, tragacanth, methylcellulose, sodium carboxymethyl-cellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution in polyethylene glycol and/or propylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Formulations for topical application, e.g., for use in treating hyperproliferative skin diseases, may include the above liquid forms, creams, aerosols, sprays, dusts, powders, lotions and ointments which are prepared by combining an active ingredient according to this invention with conventional pharmaceutical diluents and carriers commonly used in topical dry, liquid, cream and aerosol formulations. Ointment and creams may, for example, be formulated with an aqueous or oily base with the addition of suitable thickening and/or gelling agents. Such bases may, thus, for example, include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

Lotions may be formulations with an aqueous or oily base and will, in general, also include one or more of the following, namely, stabilizing agents, emulsifying agents, dispersing agents, suspending agents, thickening agents, coloring agents, perfumes and the like.

Powders may be formed with the aid of any suitable powder base, e.g, talc, lactose, starch, etc. Drops may be formulated with an aqueous base or nonaqueous base also comprising one or more dispersing agents, suspending agents, solubilizing agents, etc.

The topical pharmaceutical compositions according to the invention may also include one or more preservatives or bacteriostatic agents, e.g, methyl hydroxybenzoate, propyl hydroxybenzoate, chlorocresol, benzalkonium chlorides, etc.

The topical pharmaceutical compositions according to the invention may also contain other active ingredients such as antimicrobial agents, particularly antibiotics, anesthetics, analgesics and antipruritic agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these in packaged form.

The quantity of active compound contained in a unit dose of preparation may be varied or adjusted from about 0.01 mg to about 100 mg according to the particular application and the potency of the active ingredient. The compositions can, if desired, also contain other therapeutic agents.

The dosages may be varied depending upon the requirements of the patient, the severity of the condition being treated and the particular compound being employed. Determination of the proper dosage for a particular situation is within the skill of the art. Generally, treatment is initiated with smaller dosages which are less than the optimum dose of the compound.

Generally the recommended regimen is a dosage range of from about 1 milligram per kilogram of body weight per day to about 50 milligrams per kilogram of body weight per day in divided doses taken at about 4 hour intervals. The dosage may be increased by small increments until the optimum effect under the circumstances is reached.

The following reaction scheme illustrates the preparation of many of the compounds of the present invention:

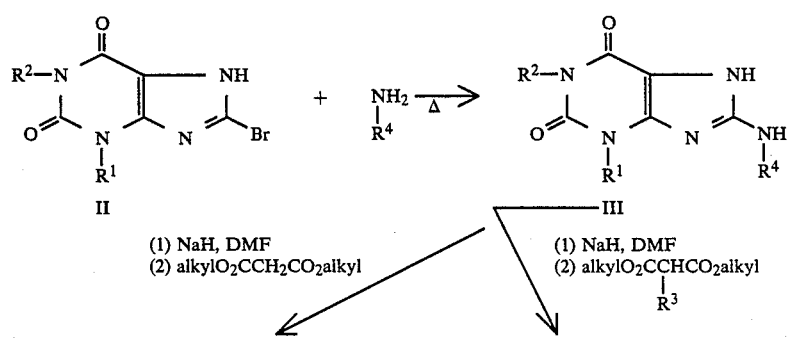

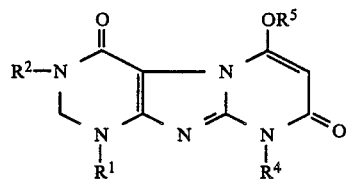
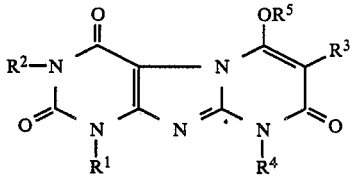

IV
(1) NH(SiMe₃)₂, (NH₄)₂SO₄
(2) LiBH₄, dioxane, Δ or
    SDMA/toluene, Δ

V
(1) NH(SiMe₃)₂, (NH₄)₂SO₄
(2) LiBH₄, dioxane, Δ or
    SDMA/toluene, Δ

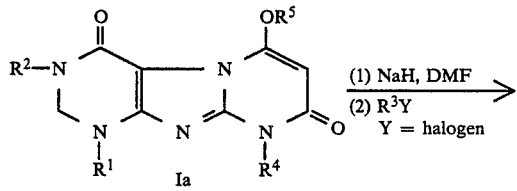
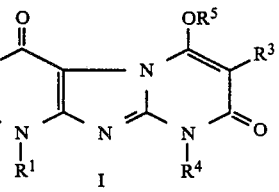

(1) NaH, DMF
(2) R³Y   Y = halogen

Ia     I wherein $R^1$, $R^2$, $R^3$, $R^4$ and $R^5$ are as defined above. Some groups, especially in $R^3$, may be sensitive to the step of reduction, and compounds containing such $R^3$ groups are better prepared by reduction of compounds of the formula IV wherein $R^3$ is hydrogen followed by introduction of the group $R^3$ under basic alkylation conditions.

When the desired substituents at $R^1$, $R^2$, $R^3$ and/or $R^4$ are not sensitive to lithium borohydride reduction, the $R^3$-substituted-2-desoxy compounds (I) may be prepared by direct reduction of the corresponding $R^3$-substituted-2-oxo compounds (V).

The intermediates of the invention having structural formula IV or V wherein $R^5$=H and

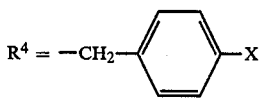

where X=H or F may be prepared by reacting a correspondingly substituted compound having structural formula III with a dialkylmalonate or substituted dialkylmalonate, respectively, in the presence of a stoichiometric amount of a base such as sodium hydride at an elevated temperature. Also the above defined intermediates of formula IV may be prepared by reacting the above defined compound of formula III with an excess of dialkylmalonate in the presence of a base such as sodium methoxide at an elevated temperature.

Compounds having structural formula III are prepared by reacting compounds having structural formula II with excess primary amine at elevated temperatures.

Compounds having structural formula I wherein $R^3$=H and $R^5$=H or a sodium cation may be alkylated to introduce the group $R^3$ (as defined above) as shown in the reaction scheme using activated electrophiles, e.g such as 3-halo alkenes, 3-halo alkynes, α-halo esters, benzyl halides, α-halo acetonitriles and the equivalents of these groups which are known in the art. The alkylations may be accomplished using sodium hydride in N,N-dimethyl formamide, triethylamine in acetone and sodium or sodium methoxide in ethanol. Phase-transfer alkylation, employing a stoichiometric quantity of tetraalkyl ammonium hydrogen sulfate in a methylene chloride-aqueous sodium hydroxide system, is also effective.

$R^5$-alkyl derivatives may be conveniently prepared by a diazoalkane reaction.

The $R^3$-unsubstituted-2-desoxy compounds (Ia) and the $R^3$-substituted 2-desoxy compounds (I) may be prepared from the corresponding 2-oxo compounds by a novel reduction process using lithium borohydride in dioxan. The reaction times for this reduction process may in may cases be reduced significantly by silylation of the tricyclic 2-oxo compounds before they undergo reduction. The compound used in the silylation step may be 1,1,1,3,3,3-hexamethyldisilazane (HMDS).

Another metal hydride which may be used in the above novel reduction process is sodium bis(2-methoxyethoxy)aluminum hydride (SDMA) in dimethoxyethanetoluene. When SDMA is used, the yield and speed of direct reduction of underivatized substrate leading to compounds having structural formulas I and Ia may be comparable to those observed with LiBH₄ on silylated substrates. However, SDMA should not be used to reduce those compounds having fluorinated aryl substituents, especially a p-fluoro phenyl group.

The intermediates of formula III may be prepared from readily available starting materials according to the sequence of steps described below.

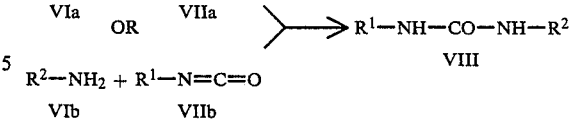

The ureas of formula VIII may be prepared by reacting approximately equimolar quantities of an amine ($R^1$—NH₂ or $R^2$—NH₂) with an isocyanate ($R^2$—N=C=O or $R^1$—N=C=O) in an inert solvent, e.g, chloroform.

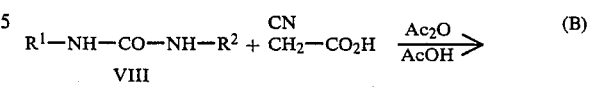

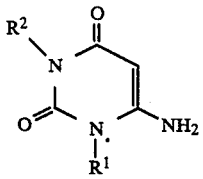

Compounds of formula IX may be prepared by the well-known Traube purine synthesis or a modification thereof. Equimolar quantities of the compound of formula VIII and cyanoacetic acid are heated to 60° C. with two equivalents of acetic anhydride using glacial acetic acid as solvent. After 2 to 8 hours as much as possible of the acetic acid (AcOH) and acetic anhydride (Ac$_2$O) are removed at 60° C. in vacuo. The resultant mixture is poured into water and made basic, e.g, with solid sodium carbonate. The mixture is boiled 1–4 hours, then cooled. On standing either a solid will form which may be filtered off and purified, or an oil will form which may be extracted and purified.

Note that, for compounds of formula VIII where R$^1$ and R$^2$ are different, two different compounds of formula IX may be formed, i.e.,

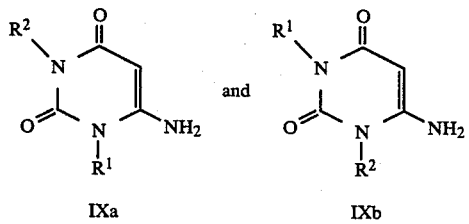

IXa    IXb

These compounds may be separated by fractional crystallization or by chromatography (e.g column or HPLC).

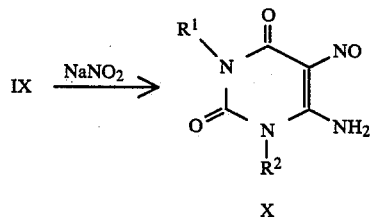

(C)

X

The purified 6-aminouracil compounds of formula IX may be converted to the 5-nitroso-6-amino-uracil compounds of formula X by combining the 6-amino-uracil derivative and sodium nitrite (one equivalent) and boiling in ethanol/water while adding glacial acetic acid. The nitroso compound of formula X which precipitates is then filtered off, washed with water and dried.

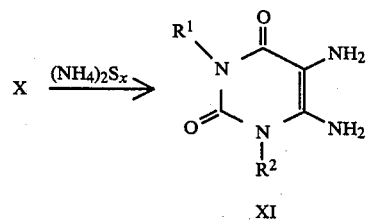

(D)

XI

The 6-amino-5-nitroso-uracil compound of formula X is reduced to the corresponding 5-aminocompound of formula XI in aqueous suspension by the use of an excess of ammonium polysulfide solution with warming When the color is discharged, the mixture is cooled and the supernatant liquid is decanted off. The residue is dissolved in methylene chloride, which is dried and evaporated. The crude product is used in the next step.

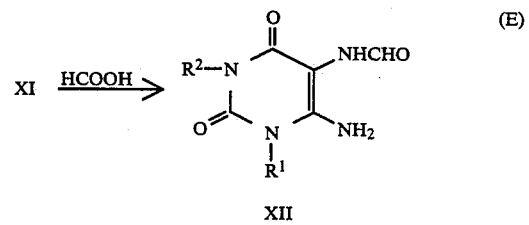

(E)

XII

The 5,6-diamino-uracil compound of formula XI is heated with excess formic acid at 120°–150° C. for 1–4 hours, then allowed to stand at room temperature overnight. Most of the acid is then removed (75° C.; reduced pressure) and the residue is dissolved in hot methanol and filtered. The product of formula XII is isolated by chilling and filtering off the resulting solid or by evaporation of the methanol.

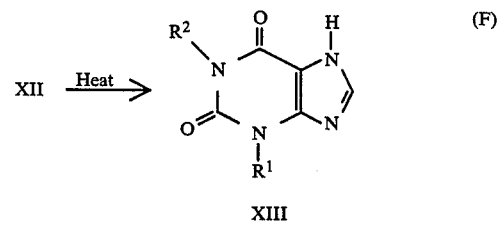

(F)

XIII

The 6-amino-5-formamido-uracil compound of formula XII is heated to 250°–285° C. until frothing ceases (10–60 mins.). The product is then cooled and the crude product of formula XIII is recrystallized, e.g from CH$_3$OH/H$_2$O.

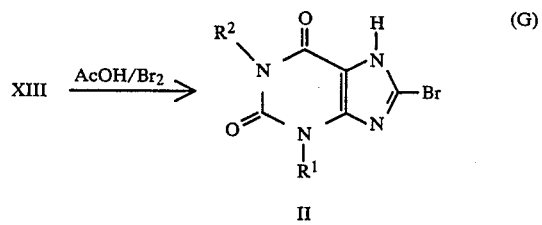

(G)

II

The xanthine compound of formula XIII is dissolved in glacial acetic acid. The solution is warmed gradually to 100° C. while a solution of bromine in acetic acid is slowly added until thin layer chromatography shows that starting material has been consumed. The product, a compound of formula II, is isolated by pouring the reaction mixture into water, filtering and rectystallizing, if necessary.

The 8-bromoxanthine of formula II is converted to the 8-substituted-amino-xanthine of formula III by heating with excess amine at elevated temperatures as described in preparative Example 1, below. An 8-chloroxanthine can be used in this reaction instead of 8-bromoxanthine if desired.

The following Preparative Examples illustrate the preparation of the starting materials.

PREPARATIVE EXAMPLE 1

8-Benzylamino-1,3-di-n-butyl-xanthine

Heat together a mixture of one equivalent of 8-bromo-1,3-di-n-butyl-xanthine and three to four equivalents of benzylamine at 160°–180° C. until thin layer chromatography shows that no starting xanthine remains. Cool. Triturate with ethanol and water to yield 8-benzylamino-1,3-di-n-butyl-xanthine.

Similarly, prepare other 8-(substituted amino)-1,3-disubstituted xanthines required for the preparation of the compounds of the present invention from the corresponding 8-bromo-(or 8-chloro)-1,3-disubstituted xanthines by heating with excess amine at elevated temperatures, in a sealed vessel, if necessary.

PREPARATIVE EXAMPLE 2A

9-Benzyl-1,3-dimethyl-7-(2-ethoxyethyl)-6-hydroxy-pyrimido[2,1-f]purine-2,4,8(1H,3H,9H)-trione (or tautomer)

To a stirred suspension of 7.43 g of 8-benzylamino-theophylline in 104 ml of dry N,N-dimethyl-formamide add portionwise over 10 minutes 1.19 g of a 60% dispersion of sodium hydride. Heat the mixture to 50° C. under a nitrogen atmosphere for 30 minutes. Add 13.30 g of the diethyl ester of β-ethoxyethylmalonic acid. Heat the mixture to 150° C. under a nitrogen atmosphere for approximately 37 hours. Allow the system to cool to room temperature and remove the solvent in vacuo. Add a mixture of water:chloroform (1:2.5) to the resulting semisolid. Acidify the aqueous portion with 3M HCl. Extract the product from the aqueous portion with chloroform. Wash the chloroform extracts with brine, dry over anhydrous sodium sulfate, filter and remove the solvent in vacuo to give the crude product. Triturate the crude product with ether. Purify the crude product by column chromatography on silica gel and triturate the major fraction with hexane to give the title compound, mp 156.5°–157.5° C.

PREPARATION EXAMPLE 2B

9-Benzyl-1,3-dimethyl-6-hydroxy-7-(n-propyl)-pyrimido[2,1-f]purine-2,4,8(1H,3H,9H)-trione (or tautomer)

Suspend 8-benzylamino-theophylline (10 g) in diethyl n-propyl-malonate (65 ml). Add sodium methoxide (0.7 g), and stir and heat to about 200° C. (bath temperature). Separate the ethanol which is formed with a Dean and Stark trap. After about 4 to 6 hours, raise the bath temperature to about 215° C. until no more starting material is present (as shown by thin layer chromatography).

Cool to below 60° C. and add ethanol. Stir and triturate and then filter, wash and air dry. Recrystallize the product from acetonitrile (about 60 parts). Wash with ether and dry in vacuo at 70° to 75° C. to yield the title compound, mp 217° C. (yield about 62%).

PREPARATIVE EXAMPLE 3

1,3-Dimethyl-9-benzyl-6-methoxy-7-(n-propyl)-pyrimido[2,1-f]purine-2,4,8(1H,3H,9H)-trione Dissolve 9-benzyl-1,3-dimethyl-6-hydroxy-7-(n-propyl)-pyrimido[2,1-f]purine-2,4,8(1H,3H,9H)-trione (3 g) in 200 ml chloroform at 0° C. and treate with an ethereal solution of diazomethane. Stir the solution at 0° for 1.5 hours and destroy the excess diazomethane by the addition of acetic acid. Wash the chloroform solution with a solution of sodium bicarbonate and remove the chloroform under reduced pressure. Chromatograph the solid obtained on silica gel using 1% methanol in chloroform to give the title compound, mp 199°–201° C.

PREPARATIVE EXAMPLE 4A

9-Benzyl-1,3-dimethyl-6-hydroxy-pyrimido[2,1-f]purine-2,4,8(1H,3H,9H)-trione Add 8-benzylaminotheophylline (30 g) and ethyl malonyl chloride (35.1 gm) to 600 ml of 1:1 dioxan-/acetonitrile. Heat the reaction mixture to reflux under a nitrogen atmosphere until the 8-benzylaminotheophylline is consumed (ca. 3.5 hrs.). Cool the reaction mixture to room temperature and pour the solution into 800 ml of ether. Filter off the precipitate. Wash the precipitate with ether and dry the product to obtain the title compound, mp. 205.5°–209° C.

PREPARATIVE EXAMPLE 4B

1,3-Dimethyl-9-(4-fluorobenzyl)-6-hydroxypyrimido[2,1-f]purine-2,4,8(1H,3H, 9H)-trione Substitute 8-(4-fluorobenzyl)aminotheophylline in the process described in Preparative Example 4A above to yield the title compound.

The following Examples illustrate the peparation of compounds of the invention. The denatured alcohol 2B used in some Examples is anhydrous ethanol denatured with 0.5% (v/v) benzene.

EXAMPLE 1A

9-Benzyl-2,3-dihydro-1,3-dimethyl-6-hydroxy-7-(propyl)pyrimido[2,1-f]purine-4,8(1H,9H)-dione A. Silylation. Reflux a mixture of 30.1 g (0.076 mole) of 9-benzyl-1,3-dimethyl-6-hydroxy-7-propyl)-pyrimido[2,1-f]purine-2,4,8(1H,3H,9H)-trione, 1.0 g of ammonium sulfate and 350 ml of 1,1,1,3,3,3-hexamethyldisilazane until the starting material dissolves, giving a cloudy solution. Distill the solvent under reduced pressure, and utilize the pinkish residual solid thus obtained directly in the reduction step "B".

B. Reduction. Dissolve the silylated product (approximately 0.076 mole) of step "A" in 1.3 liters of dry 1,4-dioxan. Place the reaction flask in a water bath at 15°–20° C., and cautiously add 9.59 g (0.442 mole) of lithium borohydride portionwise to control the resultant frothing. Heat the reaction mixture carefully (because of foaming) to 90°–95° C. and maintain that temperature with effective stirring for 78 hours (disappearance of starting material may be monitored by TLC on silica with chloroform(80)-methanol(20)-concentrated ammonium hydroxide(1)).

Remove approximately one liter of dioxane by distillation under reduced pressure, and purge the system with nitrogen as the vacuum is released. Cool the residue to room temperature, and add 1 liter of chloroform. To the stirred mixture, cautiously add portionwise 200 ml of water, followed by 180 ml of 3M hydrochloric acid, and continue stirring for 0.5 hour. Separate the layers and extract the aqueous phase with two 200-ml portions of chloroform. Dry the combined extracts over sodium sulfate, remove the drying agent by filtration and remove the solvent from the filtrate at reduced pressure. Chromatograph the solid thus obtained on silica gel, eluting first with ethyl acetate(75)-hexanes(25), then with ethyl acetate, to obtain the title compound with mp 173°–175° C. Recrystallize the above to yield the product shown in the second column of Table 1B below

TABLE 1B

| Reactant R³ = | 2,4,8-trione R⁴ = | Product 4,8-dione | Product mp °C. |
|---|---|---|---|
| —CH₂CH₂CH₃ | —CH₂—⟨C₆H₄⟩—F | 2,3-dihydro-1,3-dimethyl-9-(4-fluorobenzyl)-6-hydroxy-7-propyl-pyrimido[2,1-f]purine-4,8(1H,9H)—dione | 139–140.5° C. |
| —CH₃ | —CH₂—⟨C₆H₅⟩ | 9-benzyl-2,3-dihydro-1,3-dimethyl-6-hydroxy-7-methyl-pyrimido[2,1-f]purine-4,8(1H,9H)—dione | 222–224° C. |
| —CH₂CH₂CH₃ | —CH₂—⟨thienyl-S⟩ | 2,3-dihydro-1,3-dimethyl-9-(2-thienylmethyl)-6-hydroxy-7-propyl-pyrimido[2,1-f]purine-4,8(1H,9H)—dione | 186–188° C. | chromatographed material to obtain product with mp 177°–178.5° C.

Sodium salt. To a stirred suspension of 12.66 g (0.033 mole) of the chromatographed title compound in 1100 ml of water, add a solution of 1.33 g (0.033 mole) of sodium hydroxide in 400 ml of water. Stir for 5 hours; then filter the hazy, fine suspension through medium sintered glass. Lyophilize the clear filtrate to obtain the title salt as a solid. If the solid thus obtained is gummy, dissolve it in methanol; then remove methanol under reduced pressure, and triturate the residual solid with ether(1)-hexanes(3). Filter, and dry the product at 40° C. under vacuum to obtain the sodium salt of the title compound as a ¾ hydrate with mp 215° C. (dec.).

C. Alternatively, preparation of the title compound may be carried out as follows:

To a stirred suspension of 0.5 g (1.27 mmoles) of 9-benzyl-2,3-dihydro-1,3-dimethyl-6-hydroxy-7-propyl-pyrimido-[2,1-f]purine-2,4,8(1H,3H,9H)-trione in a mixture of 32 ml of dry dimethoxyethane and 12 ml of dry toluene, catiously add 1.5 ml (5.1 mmoles) of a 3.4M solution of sodium bis(2-methoxyethoxy)aluminum hydride in toluene. Reflux the resultant mixture under a nitrogen atmosphere for 16 hours. Remove solvent under reduced pressure, and stir the residual oil under nitrogen with 20 ml of ether and 25 ml of 1.5M hydrochloric acid. Separate the layers, and extract the aqueous phase with two 20 ml volumes of ether. Dry the combined extracts over magnesium sulfate, filter off the drying agent and remove solvent from the filtrate under reduced pressure. Purify the residual solid chromatographically, as described above, to obtain the title compound.

EXAMPLE 1B

Substitute the 2,4,8-trione compound shown in column 1 to Table 1B below for 9-benzyl-1,3-dimethyl-6-hydroxy-7-propyl-pyrimido[2,1-f]purine-2,4,8(1H,3H,9H)trione in the process of Example 1A

EXAMPLE 2A

9-Benzyl-2,3-dihydro-1,3-dimethyl-6-hydroxy-7-(3-methyl-2-butenyl)pyrimido[2,1-f]-purine-4,8(1H,9H)-dione Step A: 9-Benzyl-2,3-dihydro-1,3-dimethyl-6-hydroxy-pyrimido[2,1f]purine-4,8(1H,9H)-dione (I).

To a suspension of 395 g (1.12 moles) of 9-benzyl-1,3-dimethyl-6-hydroxy-pyrimido[2,1f]purine-2,4,8(1H,3H,9H)-trione in 10.5 liters of dry 1,4-dioxan, and 68.1 g (3.14 moles) of lithium borohydride in portions. Maintain the reaction temperature at 20°–25° C. by controlling the rate of addition and by use of a cooling bath as needed. Stri the mixture at room temperature for 0.5 hours, then reflus for 18 hours. Remove a portion of the solvent under reduced pressure, and purge the system with nitrogen as the vacuum is released. Allow the residue to cool; then add 4.5 liters of choloroform. To the resultant mixture, cautiously add dropwise 1.1-liters of water. Stir the mixture at room temperature until two clear phases result. Add 3N hydrochloric acid portionwise to bring the pH to 4–5. Separate the layers, and extract the aqueous phase with two 1.1-liter portions of cholorform. Wash the combined extracts with threee 1.1 liter volumes of water, and dry over anhydrous sodium sulfate. Filter off the drying agent, and remove volatiles from the filtrate under reduced pressure. Crystallize the residue from methanolethyl acetate to obtain title compound (I) as a solid with mp 176°–182° C.

Step B: Alkylation of I. To a suspension of 75 g (0.221 mole) of I in 4.2 liters of ethanol (anhydrous; 2B) add 12 g (0.221 mole) of sodium methoxide portionwise during about twenty minutes. To the resultant mixture add 33 g (0.221 mole) of 1-bromo-3-methyl-2-butene dropwise during 0.5 hour. Stir the reaction mixture for 18 hours at room temperature; then remove volatiles under reduced pressure. Pour the residue into 8.8 liters of cold water, saturate the aqueous phase with sodium chloride and extract with three 3-liter volumes of ether. Dry the combined extracts over anhydrous sodium sulfate, filter off the drying agent and remove solvent from the filtrate under reduced pressure. Chromatograph the residue on silica gel, eluting with ehtyl acetate (3)-hexanes(2), to obtain the title compound as a solid (mp 153°-154.5° C.).

Alternatively, the alkylation of I may be carried out in the following manner: To a slurry of 0.85 g (0.0212 mole) of 60% sodium hydride (prewashed with hexanes) in 5 ml od dry N,N-dimethylformamide, add in two portions a solution of 6.11 g (0.018 mole) of I in 125 ml of dry N,N-DMF. Stir the mixture at room temperature under a nitrogen atmosphere for 15 minutes to obtain a clear solution. Add in one portion 4.06 g (0.0273 mole) of 1-bromo-3-methyl-2-butene (mild exotherm). Stir the reaction mixture under a nitrogen atmosphere at room temperature for 4.5 hours. Pour the reaction mixture into an ice-water mixture, and extract with four 150-ml portions of chloroform. Wash the combined extracts with water, dry then over anhydrous sodium sulfate, filter, evaporate off the solvent, and chromatograph the residue on silica gel, as described above, to obtain the title compound.

EXAMPLE 2B 9-(Benzyl or substituted benzyl)-2,3-dihydro-1,3-dimethyl-6-hydroxy-7-substituted pyrimido[2,1-f]purine-4,8(1H, 9H) -diones Substitute the 2,4,8-trione compound from the first column of Table 2B below for 9-benzyl-1,3-dimethyl-6-hydroxy-pyrimido[2,1-f]purine-2,4,8[1H,3H,9H]-trione and the compound R³X for 1-bromo-3-methyl-2-butene in the process of Example 2A above to produce the substituted 4,8-dione compound in Column 2 of the Table 2B below.

TABLE 2B

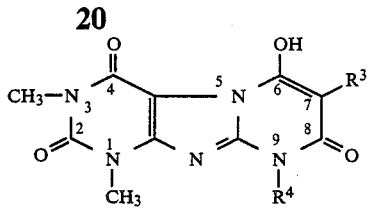

| Reactants | | Product (R₃ as in R₃X; R₄ as in trione) |
|---|---|---|
| 2,4,8 Trione R⁴ = | R³X* (X = Br) | Product M.P. °C. |
| —CH₂—C₆H₄—F | CH₂=CHCH₂Br | 131.5-133° C. |
| —CH₂—C₆H₅ | HC≡CCH₂Br | 163-164° C. |
| —CH₂—C₆H₅ | (CH₃)(H)C=C(H)(CH₂Br) | 180-183° C. |
| —CH₂—C₆H₅ | C₆H₁₁—Br (bromocyclohexane) | 208-210° C. |
| —CH₂—C₆H₅ | CH₃CH₂OCOCH₂Br | 148-150° C. |
| —CH₂—C₆H₅ | (CH₃)(CF₃)C=CHCH₂Br | 118-120° C. |
| —CH₂—C₆H₄—OCH₃ | (CH₃)₂C=CHCH₂Br | 157-159° C. |

*X is a leaving group, e.g, Br.

EXAMPLE 3

2,3-Dihydro-1,3-dimethyl-9-(4-fluorobenzyl)-6-hydroxypyrimido[2,1-f]purine-4,8(1H,9H)-dione Reflux a suspension of 395 g (1.06 moles) of 1,3-dimethyl-9-(4-fluorobenzyl)-6-hydroxy-pyrimido[2,1-f]purine-2,4,8(1H,3H,9H,)-trione, 12.32 g of ammonium sulfate and 350 ml of 1,1,1,3,3,3-hexamethyldisilazane in 4 liters of chloroform until a clear solution is obtained (18-24 hr.). Remove chloroform and excess hexamethyldisilazane under reduced pressure, and treat the residual thick gum with 9.6 liters of dry 1,4-dioxan. While stirring the resultant mixture, cautiously add 70.4 g (3.24 moles) of lithium borohydride in portions under a stream of dry nitrogen. When foaming subsides, heat the mixture to 100° C. for 18 hr. or until all starting material has been consumed (as determined by TLC on silica with chloroform(90)-methanol(10)-acetic acid(1). Remove a portion of the dioxane under reduced pressure, purge the system with nitrogen as the vacuum is released, allow the residue to cool, and add 3 liters of chloroform with stirring. Add 1.3 liters of water cautiously (because of foaming), followed by 2.3 liters of 3N hydrochloric acid. Stir for one hour; then spearate the layers. Extract the aqueous phase with two 1.3-liter volumes of chloroform, and dry the combined extracts over anhydrous sodium sulfate. Filter off the drying agent, and remove solvent from the filtrate under reduced pressure. Dissolve the residual tacky solid in 1.5 liters of boiling acetonitrile, add a small amount of decolorizing carbon, reflux for 15 minutes, and filter through a pad of Celite. Chill the filtrate, and collect the resultant crystals. Wash the crystals with cold acetonitrile, and dry them under vacuum at 50° C. to obtain the title compound, mp 214°-232° C.

When the above reduction was carried out without pretreatment of the substrate with 1,1,1,3,3,3-hexamethyldisilazane, no reaction was observed after 6 days of reflux.

EXAMPLE 4

2,3-Dihydro-1,3-dimethyl-9-(4-fluorobenzyl)-6-hydroxy-7-(3-methyl-2-butenyl)-pyrimido[2,1-f]purine-4,8(1H,9H)dione Dissolve 1.48 g (0.0644 mole) of sodium metal in 450 ml of ethanol (2B; anhydrous). Add 23.0 g (0.0644 mole) of 2,3-dihydro-1,3-dimethyl-9-(4-fluorobenzyl)-6-hydroxy-pyrimido[2,1-f]purine-4,8(1H,9H)-dione. Stir the resultant suspension under a nitrogen atmosphere for 0.5 hour, then add 9.60 g (0.0644 mole) of 1-bromo-3-methyl-2-butene. Stir the mixture at room temperature for 90 hours under a nitrogen atmosphere. Filter off the white solids, and remove solvent from the filtrate under reduced pressure. Dissolve the residue in 150 ml of chloroform, add 125 ml of 3N hydrochloric acid and shake the mixture. Separate the layers, and extract the aqueous phase with two 50-ml volumes of chloroform. Dry the combined extracts over anhydrous magnesium sulfate, filter off the drying agent, and remove solvent from the filtrate under reduced pressure. Chromatograph the residual glassy solid on silica gel, eluting with ethyl acetate(3)-hexanes(1). Triturate the product thus obtained with hexane (125 ml per gram) and filter to obtain the title compound as a solid (mp 188°–188.5° C.).

EXAMPLE 5

7,9-Dibenzyl-2,3-dihydro-1,3-dimethyl-6-hydroxypyrimido[2,1-f]purine-4,8(1H,9H)-dione To a suspension of 7.1 g (0.021 mole) of 9-benzyl-2,3-dihydro-1,3-dimethyl-6-hydroxy-pyrimido[2,1-f]purine-4,8(1H,9H)-dione in 200 ml of acetone, add 2.3 g (0.023 mole) of triethylamine, and stir the mixture for 5 minutes at room temperature under a nitrogen atmosphere to obtain a clear solution. Add dropwise to the solution 4.7 g (0.027 mole) of benzyl bromide, and reflux the mixture for 5 hours under a nitrogen atmosphere. Remove the acetone under reduced pressure, and triturate the gummy residue with methanol. Filter off the resultant white solid, pour the filtrate into water, acidify to pH 4–5 with dilute hydrochloric acid, and decant the aqueous supernatant. Dissolve the gummy residue in the chloroform, wash the solution with water, and dry over anhydrous magnesium sulfate. Remove the drying agent by filtration, and evaporate solvent from the filtrate under reduced pressure. Chromatograph the residual oil on silica gel, eluting with chloroform(96)-methanol(4), to obtain the title compound as a solid with mp 176°–179° C.

Sodium salt. Add 3.4 g (0.0074 mole) of analytically pure 7,9-dibenzyl-2,3-dihydro-1,3-dimethyl-6-hydroxypyrimido[2,1-f]purine-4,8(1H,9H)-dione to a suspension of 0.5 g (0.012 mole) of 60% sodium hydride (prewashed with three 100-ml volumes of petroleum ether) in 300 ml of dry dimethoxyethane. Stir the mixture for 30 minutes at room temperature under a nitrogen atmosphere. Filter off excess sodium hydride. Concentrate the filtrate under reduced pressure to an oil and add ether to precipitate a solid. Isolate the solid by filtration, and triturate it in fresh ether. Filter again, and dry the solid at 70° C. under reduced pressure to obtain the hemihydrate salt of the title compound as a yellow powder (mp 175°–185° C.).

EXAMPLE 6

9-Benzyl-2,3-dihydro-1,3-dimethyl-7-(N,N-dimethylamine)methenyl-6-hydroxypyrimido[2,1-f]purine-4,8(1H,9H)-dione Dissolve phosphorus oxychloride (1.5 ml=2.47 g=16.2 mmoles) in N,N-dimethylformamide (75 ml) and add portionwise the title compound of Example 2A (Part A), (5.0 g, 17.4 mmol) in dry powdered form. Stir to dissolve the solid, and allow the resultant solution to stand for 4 hours at room temperature under a nitrogen atmosphere. Remove the solvent under reduced pressure, and partition the residual oil between methylene chloride and aqueous sodium bicarbonate (frothing). Separate the phases, and wash the organic extract successively with aqueous bicarbonate, water, then brine. Dry the extract over anhydrous magnesium sulfate, remove the drying agent, and evaporate the solvent under reduced pressure. Triturate the residual solid thoroughly with ether to obtain the title product as a yellow powder, mp 235° C. (dec).

EXAMPLE 7

9-Benxyl-2,3-dihydro-1,3-dimethyl-7-formyl-6-hydroxypyrimido[2,1-f]purine-4,8-(1H,9H)-dione, sodium salt Suspend the title compound of Example 6 (4.0 g, 10.1 mmol) in 0.1N sodium hydroxide (200 ml) under a nitrogen atmosphere in a bath at 100° C. for 1 hour. Filter the mixture, and wash the material collected succesively with water, ether-isopropanol, then ether. Dry the washed solid in a vacuum pistol to obtain the title compound as a yellow powder, mp 325°–326° C. (dec).

The following formulations exemplify some of the dosage forms of the compositions of this invention. In each, the term "active compound" as used therein means 9-benzyl-2,3-dihydro-1,3-dimethyl-6-hydroxy-7-(3-methyl-2-butenyl)-pyrimido[2,1-f]purine-4,8(1H,9H)dione. It is contemplated, however, that a different compound of structural formula I could be substituted therefore, or added thereto. Consequently, the scope of the application is not to be limited by the exemplary dosage formulations contained herein.

Pharmaceutical Dosage Form Examples

EXAMPLE A

| | Tablets | | |
|---|---|---|---|
| No. | Ingredient | mg/tablet | mg/tablet |
| 1. | Active compound | 100 | 500 |
| 2. | Lactose USP 122 | 113 | |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼") if needed. Dry the damp granules. Screen the dried granules if needed and mix with Item No. 4 and mix for 10–15 minutes. Add Item No. 5 and mix for 1–3 minutes. Compress the mixture to appropriate size and weight on a suitable tablet machine.

EXAMPLE B

| No. | Ingredient | Capsules mg/capsule | mg/capsule |
|---|---|---|---|
| 1. | Active compound | 100 | 500 |
| 2. | Lactose USP 106 | 123 | |
| 3. | Corn Starch, Food Grade | 40 | 70 |
| 4. | Magnesium Stearate NF | 4 | 7 |
| | Total | 250 | 700 |

Method of Manufacture

Mix Item Nos. 1, 2 and 3 in a suitable blender for 10-15 minutes. Add Item No. 4 and mix for 1-3 minutes. Fill the mixture into suitable two-piece hard gelatin capsules on a suitable encapsulating machine.

EXAMPLE C

| Ingredient | Parenteral mg/vial | mg/vial |
|---|---|---|
| Active Compound Sterile Powder | 100 | 500 |

Add sterile water for injection or bacteriostatic water for injection, for reconstitution.

EXAMPLE D

| Ingredient | Injectable mg/vial |
|---|---|
| Active Compound | 100 |
| Methyl p-hydroxybenzoate | 1.8 |
| Propyl p-hydroxybenzoate | 0.2 |
| Sodium Bisulfite | 3.2 |
| Disodium Edetate | 0.1 |
| Sodium Sulfate | 2.6 |
| Water for Injection q.s. ad | 1.0 ml |

Method of Manufacture (for 1000 vials)
1. Dissolve p-hydroxybenzoate compounds in a portion (85% of the final volume) of the water for injection at 65°-70° C.
2. Cool to 25°-35° C. Charge and dissolve the sodium bisulfite, disodium edetate and sodium sulfate.
3. Charge and dissolve active compound.
4. Bring the solution to final volume by added water for injection.
5. Filter the solution through 0.22 membrane and fill into appropriate containers.
6. Finally sterilize the units by autoclaving

EXAMPLE E

| | Nasal Spray mg/ml |
|---|---|
| Active Compound | 10.0 |
| Phenyl Mercuric Acetate | 0.02 |
| Aminoacetic Acid USP | 3.7 |
| Sorbitol Solution, USP | 57.0 |
| Benzalkonium Chloride Solution | 0.2 |
| Sodium Hydroxide 1 N Solution to adjust pH | — |
| Water Purified USP to make | 1.0 ml |

EXAMPLE F

| Ointment Formula | mg/g |
|---|---|
| Active Compound | 1.0–20.0 |
| Benzyl Alcohol, NF | 20.0 |
| Mineral Oil, USP | 50.0 |
| White Petrolatum, USP to make | 1.0 g |

Method of Manufacture

Disperse active compound in a portion of the mineral oil. Mix and heat to 65° C., a weighed quantity of white petrolatum, the remaining mineral oil and benzyl alcohol, and cool to 50°-55° C. with stirring Add the dispersed active compound to the above mixture with stirring Cool to room temperature.

EXAMPLE G

| Cream Formula | mg/g |
|---|---|
| Active Compound | 1.0–20.0 |
| Stearic Acid, USP | 60.0 |
| Glyceryl Monostearate | 100.0 |
| Propylene Glycol, USP | 50.0 |
| Polyethylene Sorbitan Monopalmitate | 50.0 |
| Sorbitol Solution, USP | 30.0 |
| Benzyl Alcohol, NF | 10.0 |
| Purified Water, USP to make | 1.0 g |

Method of Manufacture

Heat the stearic acid, glyceryl monostearate and polyethylene sorbitan monopalmitate to 70° C. In a separate vessel, dissolve sorbital solution, benzyl alcohol, water, and half quantity of propylene glycol and heat to 70° C. Add the aqueous phase to oil phase with high speed stirring Dissolve the active compound in remaining quantity of propylene glycol and add to the above emulsion when the temperature of emulsion is 37°-40° C. Mix uniformly with stirring and cool to room temperature.

While the present invention has been described in conjunction with the specific embodiments set forth above, many aternatives, modifications and variations thereof will be apparent to those of ordinary skill in the art. All such variations and alternatives fall within the spirit and scope of the present invention, and the scope of the claims is not to be limited thereby.

We claim:

1. A method of treating hyperproliferative skin disease in a mammal comprising administering an antihyperproliferative skin disease effective amount of a compound having the structural formula I

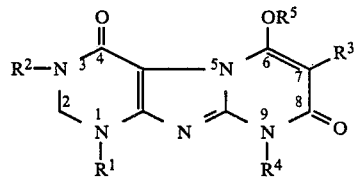

a tautomer, pharmaceutically accaptable salt, solvate or hydrate thereof, wherein:

$R^1$ and $R^2$ are each independently hydrogen, cycloalkyl having from 3 to 8 carbon atoms, phenyl, lower alkyl, substituted phenyl and lower alkyl substituted with cycloalkyl having from 3 to 8 carbon atoms, phenyl, thienyl or substituted phenyl;

$R^3$ is hydrogen, formyl, cycloalkyl having from 3 to 8 carbon atoms, alkenyl having from 2 to 8 carbon atoms (which may be substituted with up to 6 fluorines), alkynyl having from 3 to 8 carbon atoms, cycloalkenyl having from 5 to 8 carbon atoms, acyloxyalkyl having from 2 to 12 carbon atoms, —X—$R^6$ {wherein X is O, N or S and $R^6$ is phenyl, substituted phenyl, lower alkyl, or lower alkyl substituted with phenyl or cycloalkyl having from 3 to 8 carbon atoms}, —alkyl—Y—$C_pH_{2p+1}$ (wherein the alkyl portion has 1 to 6 carbon atoms, p is an integer form 0 to 4, and Y represents CO, O, S, $S^+$—$O^-$, $SO_2$ or —$NHC_rH_{2r+1}$ where r is an integer from 0 to 4), —$(CH_2)_n$—$CONR^7R^8$ (wherein $R^7$ and $R^8$ are independently hydrogen or lower alkyl and n is an integer form 0 to 6), —$(CH_2)_m$—$COOR^9$ (wherein $R^9$ is hydrogen or lower alkyl and m is an integer form 0 to 6), phenyl, substituted phenyl, lower alkyl, or substituted lower alkyl, {substituted with hydroxy, sulfhydryl, cyano, amino, halo, cycloalkyl having from 3 to 8 carbon atoms, phenyl, thienyl or substituted phenyl};

$R^4$ is hydrogen, phenyl, alkylphenyl, thienyl, substituted thienyl, pyridinyl, substituted benzyl, substituted phenyl or substituted lower alkyl {substituted with cycloalkyl having from 3 to 8 carbon atoms, phenyl, pyridinyl, thienyl or substituted phenyl}; and $R^5$ is hydrogen or alkyl having from 1 to 4 carbon atoms.

2. The method of claim 1 wherein the compound administered is of formula I or a pharmaceutically acceptable salt thereof, wherein $R^1$ and $R^2$ are independently selected from alkyl having from 1 to 4 carbon atoms;

$R^3$ is hydrogen, akenyl having from 2 to 8 carbon atoms which may be substituted with up to 6 fluorines, alkynyl having from 3 to 8 carbon atoms, cycloalkenyl having form 5 to 8 carbon atoms, lower alkyl, or lower alkyl substituted with phenyl;

$R^4$ is lower alkyl substituted with phenyl, thienyl or substituted phenyl; and $R^5$ is hydrogen or a pharmaceutically acceptable cation.

3. The method of claim 1 wherein $R^1$ and $R^2$ are alkyl having 1 to 3 carbon atoms.

4. The method of claim 3 wherein $R^1$ and $R^2$ are methyl.

5. The method of claim 4 wherein $R^3$ is hydrogen, alkenyl having from 3 to 8 carbon atoms which may be substituted with up to 6 fluorines, alkynyl having from 3 to 8 carbon atoms, cycloalkenyl having from 5 to 8 carbon atoms, lower alkyl, or lower alkyl substituted with phenyl.

6. The method of claim 5 wherein $R^3$ is hydrogen, methyl, n-propyl, 2-propynyl, 2-propenyl, trans-2-butenyl, 2-cyclohexenyl, —$CH_2CH=C(CH_3)_2$, —$CH_2CH=C(CF_3(CH_3)$, —$CH_2CH=C(CF_3)_2$ or benzyl.

7. The method of claim 6 wherein $R^4$ is benzyl, 2-thienylmethyl or substituted benzyl.

8. The method of claim 7 wherein $R^4$ is benzyl or p-fluorobenzyl.

9. The method of claim 1 wherein the compound administered has the name:
9-benzyl-2,3-dihydro-1,3-dimethyl-6-hydroxy-7-propyl-pyrimido[2,1-f]purine-4,8(1$\underline{H}$, 9$\underline{H}$)-dione;
2,3-dihydro-1,3-dimethyl-9-(4-fluorobenzyl)-6-hydroxy-7-propyl-pyrimido[2,1-f]purine-4,8(1$\underline{H}$, 9$\underline{H}$)-dione;
9-benzyl-2,3-dihydro-1,3-dimethyl-6-hydroxy-7-(3-methyl-2-butenyl)-pyrimido[2,1-f]purine-4,8(1$\underline{H}$, 9$\underline{H}$)-dione;
9-benzyl-2,3-dihydro-1,3-dimethyl-6-hydroxypyrimido[2,1-f]purine-4,8(1$\underline{H}$, 9$\underline{H}$)-dione;
2,3-dihydro-1,3-dimethyl-9-(4-fluorobenzyl)-6-hydroxy-7-(3-methyl-2-butenyl)-pyrimido[2,1-f]purine-4,8(1$\underline{H}$, 9$\underline{H}$)-dione;
9-benzyl-2,3-dihydro-1,3-dimethyl-6-hydroxy-7-methylpyrimido[2,1-f]purine-4,8(1$\underline{H}$, 9$\underline{H}$)-dione;
2,3-dihydro-1,3-dimethyl-9-(4-fluorobenzyl)-6-hydroxypyrimido[2,1-f]purine-4,8(1$\underline{H}$, 9$\underline{H}$)-dione;
7,9-dibenzyl-2,3-dihydro-1,3-dimethyl-6-hydroxypyrimido[2,1-f]purine-4,8(1$\underline{H}$, 9$\underline{H}$)-dione;
9-benzyl-2,3-dihydro-1,3-dimethyl-7-formyl-6-hydroxypyrimido[2,1-f]purine-4,8(1$\underline{H}$, 9$\underline{H}$)-dione;
2,3-dihydro-1,3-dimethyl-)]1 -(4-fluorobenzyl)-6-hydroxy-7-(2-propenyl)-pyrimido[2,1-f]purine-4,8(1$\underline{H}$, 9$\underline{H}$)-dione;
9-benzyl-2,3-dihydro-1,3-dimethyl-7-(2-propynyl)-6-hydroxy-pyrimido[2,1-f]purine-4,8(1$\underline{H}$, 9$\underline{H}$)-dione;
9-benzyl-7-(trans-2-butenyl)-2,3-dihydro-1,3-dimethyl-6-hydroxy-pyrimido[2,1-f]purine-4,8(1$\underline{H}$, 9$\underline{H}$)-dione;
9-benzyl-7-(3-cyclohexenyl)-2,3-dihydro-1,3-dimethyl-6-hydroxy-pyrimido[2,1-f]purine-4,8(1$\underline{H}$, 9$\underline{H}$)-dione;
9-benzyl-2,3-dihydry-1,3-dimethyl-7-(ethoxy carbonylmethyl)-6-hydroxy-pyrimido[2,1-f]purine-4,8(1$\underline{H}$, 9$\underline{H}$)-dione;
9-benzyl-1,3-dimethyl-6-hydroxy7-(3-trifluoromethyl-2-butenyl)-2,3-dihydropyrimido[2,1-f]purine-4,8[1$\underline{H}$, 9$\underline{H}$)-dione;
2,3-dihydro-1,3-dimethyl-9-(2-thienylmethyl)-6-hydroxy-7-propyl-pyrimido[2,1-f]purine-4,8(1$\underline{H}$,9$\underline{H}$)-dione; or
2,3-dihydro-1,3-diemthyl-9-(4-methoxybenzyl)-6-hydroxy-7-(3-methyl-2-butenyl)-pyrimido[2,1-f]purine-4,8(1$\underline{H}$, 9$\underline{H}$)-dione.

10. A method of treating hyperproliferative skin disease in a mammal comprising administering an antihyperproliferative skin disease effective amount of a compound of formula I which is:
9-benzyl-2,3-dihydro-1,3-dimethyl-6-hydroxy-7-(3-methyl-2-butenyl)-pyrimido[2,1-f]purine-4,8(1$\underline{H}$, 9$\underline{H}$)-dione.

11. The method of claim 1 wherein the compound is administered topically.

* * * * *